United States Patent
Ribbing et al.

(10) Patent No.: US 8,320,519 B2
(45) Date of Patent: Nov. 27, 2012

(54) MULTI-SOURCE ENCODED X-RAY IMAGING

(75) Inventors: Carolina M. Ribbing, Aachen (DE);
Gereon Vogtmeier, Aachen (DE);
Roland Proksa, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 829 days.

(21) Appl. No.: 12/305,492

(22) PCT Filed: Jun. 13, 2007

(86) PCT No.: PCT/US2007/071101
§ 371 (c)(1),
(2), (4) Date: Dec. 18, 2008

(87) PCT Pub. No.: WO2007/149751
PCT Pub. Date: Dec. 27, 2007

(65) Prior Publication Data
US 2011/0311019 A1 Dec. 22, 2011

Related U.S. Application Data (60) Provisional application No. 60/805,515, filed on Jun. 22, 2006.

(51) Int. Cl.
*A61B 6/00* (2006.01)
(52) U.S. Cl. .................. 378/9; 378/7; 382/131
(58) Field of Classification Search .......... 378/7, 9
See application file for complete search history.

(56) References Cited

U.S. PATENT DOCUMENTS

| | | | |
|---|---|---|---|
| 5,602,893 A * | 2/1997 | Harding | 378/86 |
| 2003/0128801 A1 | 7/2003 | Eisenberg et al. | |
| 2004/0079232 A1 | 4/2004 | Groh et al. | |
| 2004/0114710 A1 | 6/2004 | Ozaki | |
| 2004/0213371 A1 | 10/2004 | Bruder et al. | |
| 2004/0213378 A1 | 10/2004 | Zhou et al. | |
| 2004/0228442 A1 * | 11/2004 | Sakaguchi et al. | 378/87 |
| 2005/0148857 A1 | 7/2005 | Maki et al. | |

(Continued)

FOREIGN PATENT DOCUMENTS

WO 2007088497 A1 8/2007

OTHER PUBLICATIONS

Cula, et al.; Polarization Multiplexing for Bidirectional Imaging; 2005; IEEE Proc. on Computer Vision and Pattern Recognition; 8 pages.

(Continued)

*Primary Examiner* — Alexander H Taningco (57) ABSTRACT

A tomographic apparatus (10) includes at least two x-ray sources (16) that are concurrently driven with different switching patterns to generate uniquely encoded radiation. The tomographic apparatus (10) further includes at least two detectors (20) that each detect primary radiation emitted by its corresponding one of the at least two x-ray sources (16) and cross scatter radiation from at least one of the other at least two x-ray sources (16). Each of the at least two detectors (20) produces an aggregate signal representative of the detected primary and cross scatter radiation. The tomographic apparatus (10) further includes a decoupler (30) which, based on the different switching patterns, identifies at least one signal corresponding to at least one of the at least two x-ray sources (16) within the aggregate signal and associates the identified signal with its corresponding x-ray source (16).

24 Claims, 4 Drawing Sheets

U.S. PATENT DOCUMENTS

2005/0197583 A1    9/2005   Chance
2005/0228291 A1   10/2005   Chance
2006/0023832 A1    2/2006   Edic et al.
2007/0253525 A1*  11/2007   Popescu ............................ 378/7
2009/0116612 A1*   5/2009   Ziegler ............................. 378/9
2009/0207968 A1*   8/2009   Grass ............................... 378/9
2009/0279659 A1*  11/2009   David et al. ..................... 378/7

OTHER PUBLICATIONS

Everdell, et al.; A frequency multiplexed near infra-red topography system for imaging functional activation in the brain; 2004; OSA Biomedical Topic Meetings; 3 pages.

Johns, P.C., et al.; Medical x-ray imaging with scattered photons; 2002; SPIE Regional Meeting on Optoelectronics, Photronics and Imaging; SPIE TD01; p. 355-357.

McIlraith, A. H.; A soft x-ray spectrometer with pulsed source, and synchronous phosphor-photomultiplier detector; 1962; Sci. Instrum.; vol. 39; pp. 504-508.

Yu, et al.; Frequency-domain multiplexing system for in vivo diffuse light measurements of rapid cerebral hemodynamics; 2003; Applied Optics; 42(16)2931-2939.

Yue, et al.; Generation of continuous and pulsed diagnostic imaging x-ray radiation using a carbon-nanotube-based field-emission cathode; 2002; Applied Physics Letters; 81(2)355-357.

Zhang, et al.; Stationary scanning x-ray source based on carbon nanotube field emitters; 2005; Applied Physics Letters; vol. 86; 3 pages.

* cited by examiner

MULTI-SOURCE ENCODED X-RAY IMAGING

CROSS REFERENCE TO RELATED APPLICATIONS

This application claims the benefit of U.S. provisional application Ser. No. 60/805,515 filed Jun. 22, 2006, which is incorporated herein by reference.

The following relates to imaging systems. It finds particular application to computed tomography (CT) and, more particularly to processing concurrently detected radiation from different x-ray sources.

With conventional single x-ray tube CT systems, the x-ray tube limits the performance of the system. In particular, heat dissipation in the anode of the x-ray tube is one factor restricting tube power. The tube can be operated at less than 100% duty cycle to facilitate anode heat dissipation; however, this results in less efficient use of the tube and a reduction in the photon flux, and high photon fluxes are desired for imaging transient processes such as with cardiac CT.

With dual tube CT systems, photon flux can be increased by using both tubes. These systems are operated such that either both tubes are concurrently generating and emitting x-rays or only one of the tubes is generating and emitting x-rays at any given time where the tubes are alternately activated. With concurrent operation, the detectors corresponding to each tube also detect primary radiation and radiation from the other tubes (cross scatter). Thus, the aggregate scatter detected by any set of detectors increases relative to single tube use. Alternating tubes mitigates cross scatter, but it reduces photon emission for each tube per unit of time based on the number of tubes. As a result, acquisition time increases and tube power has to increase to achieve a similar signal-to-noise ratio (SNR). Alternating tubes is also inefficient in that each tube is on for only a fraction of the time.

In view of the foregoing, there is an unresolved need for improved systems and methods that overcome the above and/or other deficiencies of conventional systems.

Aspects of the present invention address these matters, and others.

According to one aspect, a tomographic apparatus is illustrated. The tomographic apparatus includes at least two x-ray sources, at least two detectors, and a decoupler. The at least two x-ray sources can be concurrently driven with different switching patterns to generate uniquely encoded radiation. Each detector detects primary radiation emitted by its corresponding one of the at least two x-ray sources and cross scatter radiation from at least one of the other at least two x-ray sources. Upon detecting radiation, each of the at least two detectors produces an aggregate signal representative of the detected primary and cross scatter radiation. A decoupler, based on the different switching patterns, identifies at least one signal corresponding to at least one of the at least two x-ray sources within the aggregate signal and associates the identified signal with its corresponding x-ray source.

Figure 1:
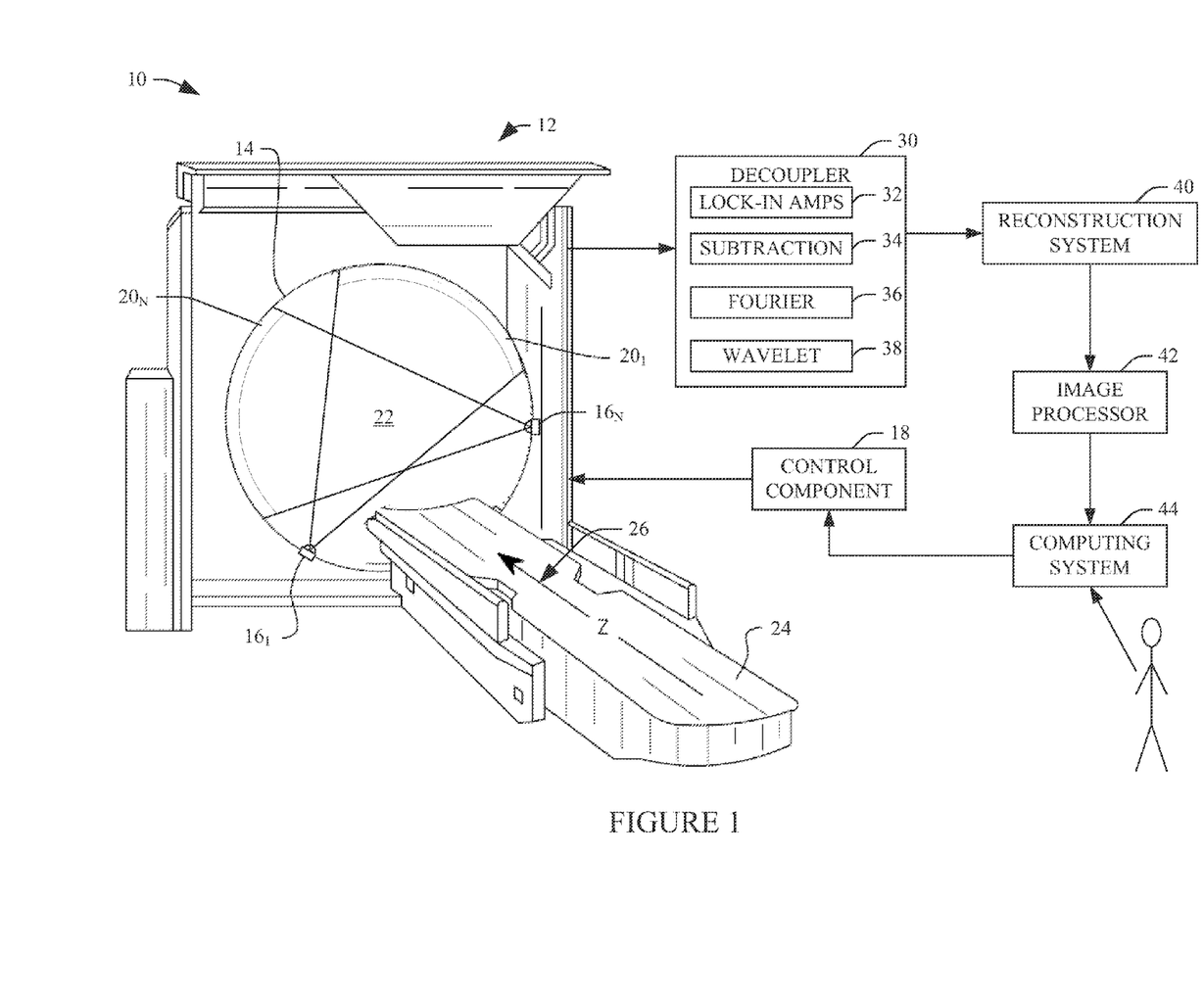
FIG. 1 illustrates an exemplary imaging system with a plurality of concurrently driven x-ray sources that generate encoded x-ray beams.

With reference to FIG. 1, a imaging system 10 is illustrated. The imaging system 10 can be a medical imaging system, an animal imaging system, an industrial imaging system, etc. The imaging system 10 employs multiple concurrently activated x-ray sources to irradiate a portion of a subject being imaged. The radiation emitted by each source is uniquely encoded (e.g., via frequency, code, phase, amplitude, and/or duty cycle encoding). A radiation detector detects primary radiation emitted by a corresponding source and cross scatter radiation emitted by other sources and generates an aggregate signal, which includes signal components indicative of the detected primary and cross scatter radiation. The unique encoding of the radiation can be used to decouple or otherwise extract one or more of the individual signal components from the aggregate signal. In one non-limiting aspect, this may be used to increase temporal resolution of the acquired images, reduce the rotational speed of the gantry, simplify the mechanical construction, provide faster imaging relative to conventional alternatively mode x-ray tube approaches, and/or reduce cross-scatter relative to conventional simultaneous mode approaches.

The imaging system 10 includes a CT scanner 12 having a rotating gantry 14 that supports N x-ray sources $16_1$, $16_N$ (collectively referred to herein as x-ray sources 16), wherein N is an integer equal to or greater than two. The x-ray sources 16 are disposed about the gantry 14 with an angular offset (e.g., for two sources, 90 degrees+0.5*Fan-angle) from each other. Each of the x-ray sources 16 can include grids, gates, shutters, and/or the like to create the uniquely encoded switching patterns. In one implementation, the x-ray sources 16 are implemented as grid controlled x-ray tubes, in which the grids serve to modulate or otherwise control the output of the respective tube according to the desired switching pattern. For example, the grids can be used to switch each of the x-ray sources 16 "on" and "off" according to the desired encoding pattern. The use of other suitable electrical control circuits or other mechanisms that provide the desired encoding is also contemplated. An example of a suitable alternative to conventional x-ray tubes with thermal cathodes (filaments) is an x-ray source incorporating field emitting cathodes such as "cold cathodes," which typically allow higher frequency pulsed emission, e.g. at 100 kHz, as described in *Generation of continuous and pulsed diagnostic imaging x-ray radiation using a carbon-nanotube-based field-emission cathode*, G. Z. Yue et al, *Appl. Phys. Lett.*, Vol. 81, No. 2, 8 Jul. 2002, which is incorporated by reference herein.

A control component 18 sends control signals or other commands to the x-ray sources 16 to uniquely encode the radiation generated by the various sources 16. In one implementation, frequency encoding is used so that the various sources 16 are driven at different switching frequencies. In addition to frequency encoding, other encoding techniques such as code, phase, amplitude, and duty cycle encoding (either alone or in various combinations) are contemplated. Such encoding is performed so that two or more of the x-ray sources 16 can be concurrently operated to simultaneously emit radiation. In one instance, the various switching patterns are generated by a common oscillator, which mitigates relative frequency drift between individual x-ray sources 16.

The gantry 14 also supports sets of x-ray sensitive detectors $20_1$ and $20_N$ (collectively referred to herein as set of x-ray sensitive detectors 20). Each set of the x-ray sensitive detectors 20 is disposed about the gantry 14 to subtend an angular arc opposite its corresponding one of the x-ray sources 16 to define an imaging region 22 therebetween. The detectors 20 can be based on various detector technologies. For example, in one instance at least one detector uses indirect conversion (e.g., incorporating a gadolinium oxysulphide (GOS) scintillator) technology. In another instance, at least one detector uses direct conversion (e.g., incorporating crystalline cadmium zinc telluride (CZT)) technology.

In another embodiment, several x-ray sources 16 in a medical imaging system 10 are mounted on a stationary frame surrounding the portion of the subject being imaged, e.g. as described in Computed tomography system for imaging of human and small animal, Zhou et al, US2004/0213378 A1, or as described in Imaging apparatus using distributed x-ray sources and method thereof C. Ribbing et al, EP 06101175.5 (filed Feb. 2, 2006), both of which are incorporated by reference herein. Such an imaging system typically is less complex in construction, but may require a larger number of x-ray sources 16 and/or x-ray sensitive detectors 20 to achieve images of the same quality as in the rotating set-up.

A subject (or patient) support 24 supports a subject such as a human within an imaging region 22. The support 24 may be movable in order to allow an operator to guide the subject to a suitable location within the imaging region 22 before, during and/or after performing a helical, axial, and/or other scan, for example, by moving the support 24 along a z-axis 26. While the system 10 has been described as a third generation CT system, other configurations are contemplated. For example, fourth generation systems having one or more stationary detector rings are also contemplated. In such an implementation, the detectors of the detector ring that correspond to a particular x-ray source would vary as a function of the angular position of the source.

When two or more of the x-ray sources 16 are operated concurrently, each set of detectors 20 respectively detects radiation emitted by its corresponding one of the x-ray sources 16 and the other x-ray sources 16. Thus, for a particular set of detectors 20, e.g., $20_1$, the detected radiation includes radiation emitted by its x-ray source $16_1$ (primary radiation and forward scattered radiation) as well as radiation emitted by the x-ray source $16_N$ (cross scatter). Each detector generates an aggregate signal that includes signal components of both the primary and cross scatter radiation.

The signal from the various detectors 20 is provided to a decoupler 30 that extracts one or more of the individual signals from the aggregate signal generated by each detector 20. In one implementation suitable for use with frequency encoded signals, lock-in amplifiers 32 are used to "lock-in" on one or more of the signals and according reference pattern/ modulation frequency within the aggregate signal. When using the lock-in amplifiers 32, both the aggregate signal and the switching pattern, via a SYNC connection 31, that corresponds to a signal of interest are provided to the lock-in amplifier 32. The lock-in amplifier 32 multiplies the aggregate signal by one of the switching patterns. For this example, assume the aggregate signal is multiplied by the switching pattern corresponding to the signal indicative of the radiation from the source $16_1$.

The product of the aggregate signal and the switching pattern is processed by a low pass filter, a band pass filter centered about the frequency of the switching pattern or the like. The filter passes constant components and suppresses time-varying components. Since the signal encoded with the switching pattern and the switching pattern have the same frequency, the signal corresponding to the source $16_1$ is recovered. Since the other uniquely encoded signals are associated with a frequency different than this switching pattern, they are suppressed. The signal uniquely encoded with the switching pattern corresponding to the source $16_N$ can similarly be obtained by multiplying the aggregate signal by the appropriate switching pattern.

Using the lock-in amplifier 32, the aggregate signal is demultiplexed and the intensity contribution of one or more of the signals within the aggregate signal can be identified and associated with or pin-pointed to its corresponding one of the sources 16. Where the objective is to account for scatter radiation in the case of concurrently operating x-ray sources 16, at least one of the lock-in amplifiers 32 can be provided for each of the detectors 20 and used to extract the signal component produced by the detectors' respective x-ray sources 16. In other applications, the ability to pin-point the source of scattered radiation may facilitate scatter imaging and/or multi-modality set-ups using e.g. transmission and scatter tomography.

In scatter imaging, scattered photons in both forward and backward direction can be used for image reconstruction. The backscatter is dominated by Compton (incoherent) scatter, which is sensitive to the number of electrons per unit volume. Forward scatter is largely coherent scatter, which is the basis of x-ray diffraction and gives a fingerprint of molecular structure. Its cross section varies with photon energy and angle in a material-specific way, also for amorphous materials. Scatter dependence on atomic composition and molecular structure makes it useful for distinguishing tissues within a patient. Therefore, in medical imaging, scattered radiation can also be an additional source of information.

For some imaging tasks, contrast and SNR can be improved at unchanged radiation dose by collecting and analyzing a portion of the scatter, see e.g. *Medical x-ray imaging with scattered photons*, P. C. Johns, R. C. Leclair, M. P. Wismayer, *SPIE Regional Meeting on Optoelectronics, Photonics, and Imaging, SPIE TD*01, p. 355-357 (2002), which is incorporated by reference herein. Using the present invention, the unique encoding of the radiation can be used to extract one or more of several individual signal components from an aggregate signal. More specifically, the cross scatter radiation can be pin-pointed to its source of origin and/or be used to obtain additional information on the object being imaged, e.g. contributing to higher contrast and/or SNR and/ or providing information on atomic number or chemical structure.

Other decoupling techniques, such as subtraction 34, Fourier transforms 36, and wavelet decomposition 38, are also contemplated.

The decoupled signals are provided to a reconstruction system 40. The reconstruction system 40 reconstructs decoupled signals to generate volumetric data indicative of the scanned region of the subject. An image processor 42 processes the volumetric image data generated by the reconstruction system 40. The generated images can then be displayed, filmed, archived, forwarded to a treating clinician (e.g., emailed, etc.), fused with images from other imaging modalities, further processed (e.g., via measurement and/or visualization utilities and/or a dedicated visualization system), stored, etc.

A computing system 44 facilitates operator interaction with and/or control of the scanner 12. The computing system 44 can be a computer such as a workstation, a desktop, a tower, a laptop, or the like. Software applications executed by the computing system 44 allow the operator to configure and/or control operation of the scanner 12. For instance, the operator can interact with the computing system 44 to select scan protocols, initiate, pause and terminate scanning, view images, manipulating volumetric image data, measure various characteristics of the data (e.g., CT number, noise, etc.), etc. The computing system 44 communicates various information to the control component 18. Such information may include computer readable instructions to configure and/or control the scanner 12 for a particular scan protocol. For example, such instructions may include parameters such as x-ray tube voltage, current, pulse frequency, phase, amplitude, duty cycle, etc., decoupling, demultiplexing algorithm, etc. The control component 18 uses such information as described above to control the scanner 12.

Figure 2:
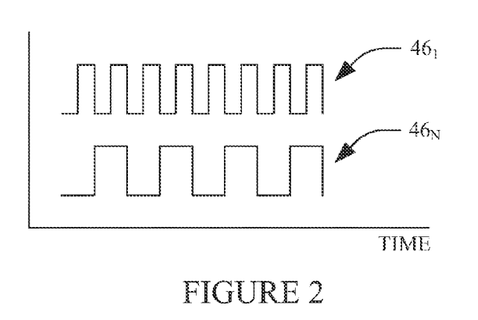
FIG. 2 illustrates exemplary switching patterns for uniquely frequency encoding the radiation emitted by concurrently driven x-ray sources.

As previously discussed, a different switching pattern can be used for each of the x-ray sources 16 in order to uniquely encode each of the sources 16. Turning now to FIG. 2, an exemplary frequency encoding scheme will be described in relation to a system having two x-ray sources 16. Exemplary switching patterns $46_1$, $46_N$ (collectively referred to herein as switching patterns 46) for encoding the emitted radiation from x-ray sources $16_1$, $16_N$ are shown as a function of time. In this non-limiting example, the switching patterns 46 applied to the x-ray sources 16 have different frequencies. In one instance, at least one of the x-ray sources 16 is switched according to a unique pattern that is repeated with a certain frequency. The frequency may depend on the operation mode, a maximum data acquisition speed, and/or a gantry rotation speed. A typical frequency would be in the hundred Hz to few kHz range adapted to the maximum readout frequency of the detector system to avoid undersampling.

Figure 3:
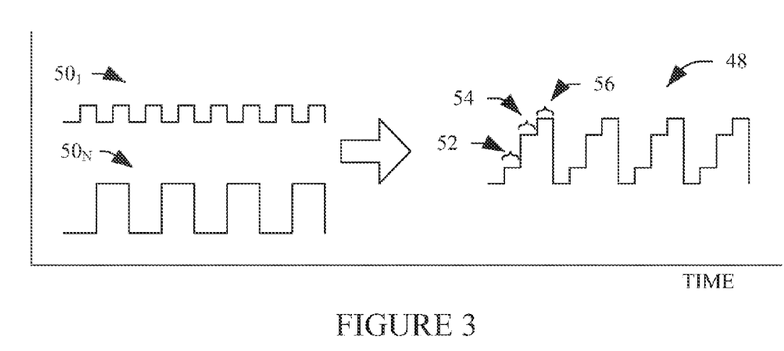
FIG. 3 illustrates an exemplary combined signal including signal components frequency encoded with different switching patterns.

FIG. 3 illustrates an exemplary combined or aggregate signal 48 generated by a detector associated with the x-ray source $16_N$. In this example, the aggregate signal 48 includes contributions from primary radiation signal $50_N$ and cross scatter radiation signal $50_1$, respectively corresponding to the switching patterns $46_N$, $46_1$. The intensity of the cross scatter radiation signal $50_1$ is less than that of the primary radiation signal $50_N$ due to the loss of intensity when scattered. The aggregate signal 48 includes a portion 52 including the cross scatter radiation signal, a portion 54 including the primary radiation signal, and a portion 56 including both the cross scatter and the primary radiation signals. Unless accounted for, the scatter contributions can deleteriously affect the quality of the reconstructed image.

Figure 4:
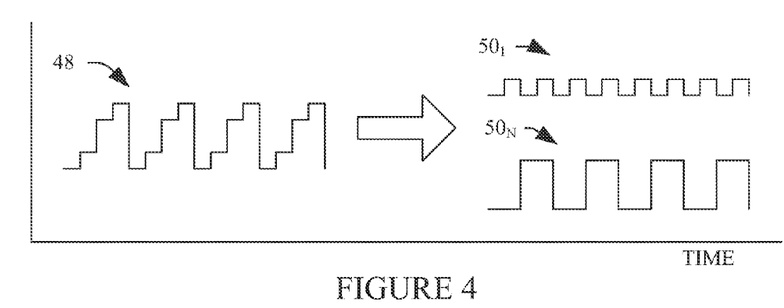
FIG. 4 illustrates a first exemplary technique for decoupling at least one signal from the aggregate signal.

FIG. 4 illustrates exemplary decoupled signals. Such decoupling can be accomplished via various techniques. For example, the lock-in amplifiers 32 can be used as described previously to lock-in on a desired signal to extract that signal from the aggregate signal 48. In this figure, the individual signals 50 are illustrated as separated signals for explanatory and clarity purposes. It is to be understood that a physical separation of each of the signals 50 from the aggregate signal 48 may or may not occur. For example, in one instance each of the signals 50 is separated from the aggregate signal 48. In another instance, one or more of the signals 50 can be identified within and/or extracted from the aggregate signal 48. In yet another instance, one or more desired ones of the signals 50 can be identified, locked on to, passed, retained, enhanced, etc. and/or one or more undesired ones of the signals 50 can be suppressed, discarded, ignored, etc. The extracted signal(s) can then be provided to the reconstruction system 40 and processed as described above.

Figure 5:
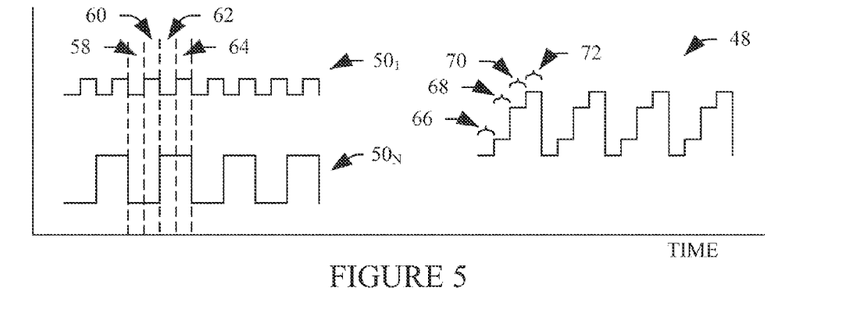
FIG. 5 illustrates another exemplary technique for decoupling at least one signal from the aggregate signal.

FIG. 5 illustrates a decoupling approach using the subtraction technique 34. When using square wave switching patterns 46, the resulting radiation signals 50 are associated with a period 58 in which neither of the sources 16 is "on," periods 60, 62 in which only one of the sources 16 is "on," and a period 64 in which both of the sources 16 are "on." The periods 58-64 are reflected in the aggregate signal 48 at 66, 68, 70 and 72, respectively, and can be used to extract one or more of the individual signals 50 from the aggregate signal 32. For example, from the aggregate signal 48 the portions at 66 and 68 can be used to identify the signal $50_1$ and $50_N$. Once identified, the signal $50_1$ can be subtracted from the aggregate signal 48 to recover the signal $50_N$, and the signal $50_N$ can be subtracted from the aggregate signal 48 to recover the signal $50_1$. The extracted signal can then be provided to the reconstruction system 40 and processed as described above.

Figure 6:
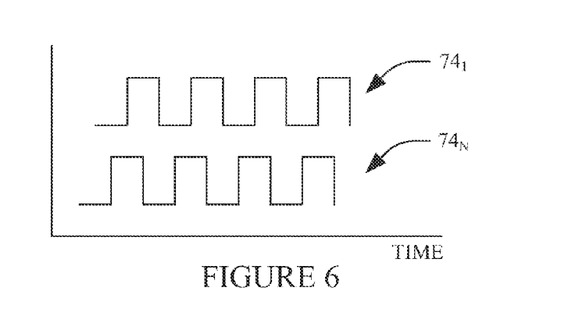
FIG. 6 illustrates exemplary switching patterns for uniquely phase encoding the radiation emitted by concurrently driven x-ray sources.
Figure 7:
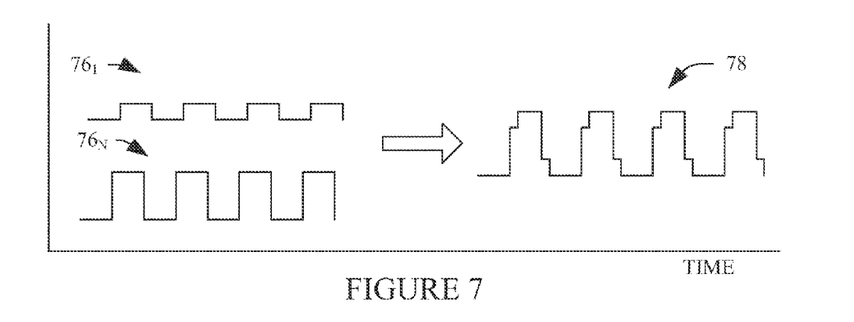
FIG. 7 illustrates an exemplary combined signal including signal components phase encoded with different switching patterns.

An alternative to the frequency encoding described above is phase encoding. FIG. 6 illustrates exemplary phase encoded patterns $74_1$ and $74_N$ (collectively referred to as phase encoded patterns 74). FIG. 7 illustrates exemplary phase encoded cross scatter radiation and primary radiation signals $76_1$, $76_N$ (collectively referred to as phase encoded radiation signals 76) respectively resulting from the phase encoded patterns $74_1$ and $74_N$. An aggregate signal 78 includes components of the phase encoded cross scatter and primary radiation signals 76. With phase multiplexing, various decoupling techniques such as Fourier and wavelet based transforms and/or other approaches can be used for signal identification and/or extraction. In addition, when using phase multiplexing the x-ray sources 16 can be operated with phase differences not limited to half a period at duty cycles greater than 50%.

In the above examples, the switching patterns 50 and 76 include trains or sequences of square pulses driven at different frequencies (the switching patterns 50) and different phases (the switching patterns 76) with duty cycles of about 50%. It is to be understood that in other instances various other pulse shapes (e.g., sinusoidal, triangular, sine, etc.), frequencies, amplitudes, phases, and/or duty cycles (greater or less) can be used. Using duty cycles greater than 50% provides for greater efficiency since each x-ray source 16 is generating and emitting radiation for more than half of the time.

When sampling the aggregate signal 48, the read-out frequency (or sampling frequency) is at least two times (2×) the highest frequency $\max(f_{switch})$ in the aggregate signal 48 (Nyquist theorem). However, in one instance since multiple superimposed signals are being resolved during signal decoupling, the read-out frequency is also a function of the minimum difference $\min(\Delta f)$ between switching frequencies. As an example, an integration time of 100 μs corresponds to 10 kHz, which could be used to resolve two multiplexed x-ray signals switched at 3 and 3.5 kHz. With conventional CT imaging, signal integration times as low as 100 μs are used because of relatively fast gantry rotation and the relatively large number of projections. In one example, a smaller min $(\Delta f)$ or a greater $\max(f_{switch})$ results in a higher sample rate (or shorter frame time). In one instance, this may allow for higher gantry rotational speeds.

Figure 8:
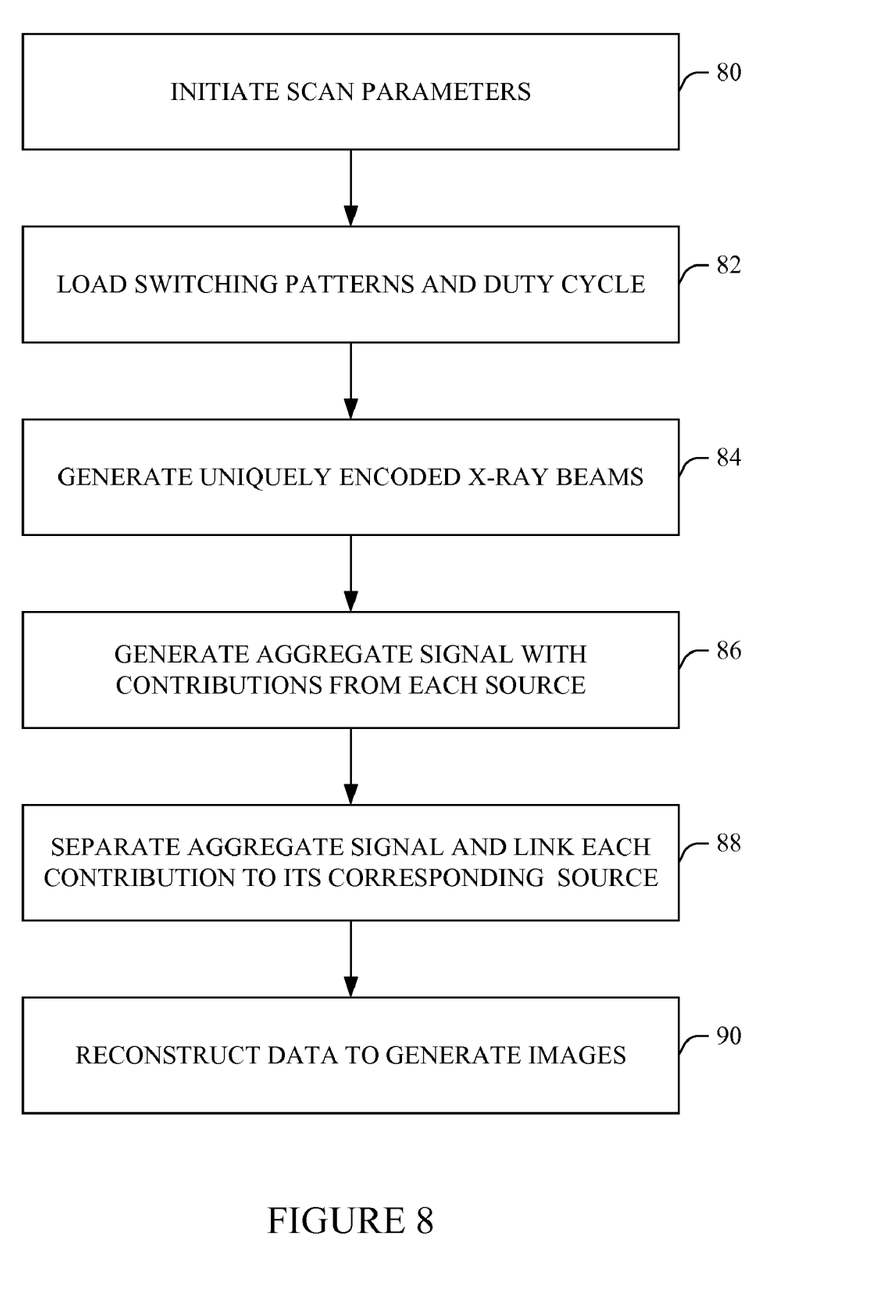
FIG. 8 illustrates an exemplary method for coupling and decoupling uniquely encoded signals corresponding to different concurrently driven x-ray sources.

FIG. 8 illustrates a non-limiting method for scanning a subject with the imaging system 10. At reference numeral 80, scan parameters are initiated. This includes interacting with scanner software applications executed by the computing system 44 to configure and/or control operation of the scanner 12 to scan a subject in the imaging region 22. At 82, the computing system 44 communicates with the controller 18, which subsequently conveys control commands to the x-ray sources 16, including radiation encoding schemes, switching patterns, duty cycle, decoupling algorithms, etc. Such schemes may be frequency, phase, amplitude, duty cycle, etc. based. Suitable switching patterns are illustrated herein. As discussed above, the duty cycle for each source 16 can be less than, equal to, or, greater then 50%, and the decoupling algorithm can be based on the lock-in amplifier 32, the subtraction 34, the Fourier 36, the wavelet 38, and/or other (e.g., frequency, phase, etc.) techniques.

At reference numeral 84, each of the x-ray sources 16 generates and emits a radiation beam uniquely encoded with its switching pattern. At 86, each detector detects the primary radiation emitted by its corresponding x-ray source 16 and the cross scatter radiation emitted by the other x-ray sources 16 and generates an aggregate signal representative of the uniquely encoded radiation as discussed herein. At 88, the aggregate signal 48 for each of the different detectors is measured and sampled (e.g., factoring in the Nyquist theorem and the minimum difference between switching frequencies), and the decoupler 30 identifies and/or extracts one or more of the individual signals from the aggregate signal 48. Using the techniques described herein, the extracted signal(s) is associated with its one of the sources 16.

At 90, the reconstruction system 40 reconstructs the primary signal, and the image processor 42 processes the reconstructed data to generate corresponding images. The images can be stored and/or provided to the computing component 44 for visual observance by the operator, filmed, further processed, etc.

The systems and/or methods described herein and/or derivations thereof can be applied in medical imaging applications such as, but not limited to, cardiac CT, animal x-ray imaging, security scanning systems, non-destructive materials analysis or defect detection, machine vision, systems incorporating distributed sources, industrial imaging, optical imaging systems, etc.

The invention has been described with reference to the preferred embodiments. Of course, modifications and alterations will occur to others upon reading and understanding the preceding description. It is intended that the invention be construed as including all such modifications and alterations insofar as they come within the scope of the appended claims.

What is claimed is:

1. A tomographic apparatus comprising:
    at least two x-ray sources that are concurrently activated to simultaneously emit radiation during a same time period but with different partially overlapping switching patterns to generate uniquely encoded radiation;
    at least two detectors, wherein each of the at least two detectors detects primary radiation emitted by a corresponding one of the at least two x-ray sources and cross scatter radiation from at least one of the other at least two x-ray sources and produces an aggregate signal including both of the detected primary radiation and the detected cross scatter radiation; and
    a decoupler which, based on the different switching patterns, extracts from at least one of the aggregate signals the detected primary radiation and associates the extracted primary radiation with the corresponding x-ray source.

2. The apparatus of claim 1 further including a reconstruction system that reconstructs the primary radiation signal to generate an image of a subject within an imaging region.

3. The apparatus of claim 1 wherein each of the different switching patterns is driven at different frequency with respect to each other to uniquely frequency encode the x-ray radiation.

4. The apparatus of claim 1 wherein the different switching patterns are code-modulated to uniquely encode the x-ray radiation.

5. The apparatus of claim 1 wherein the different switching patterns are phase shifted with respect to each other to uniquely phase encode the x-ray radiation.

6. The apparatus of claim 1 wherein at least one of the different switching patterns has a duty cycle of greater than 50%.

7. The apparatus of claim 1 wherein the different switching patterns are driven at different duty cycles with respect to each other to uniquely encode the x-ray radiation.

8. The apparatus of claim 1 wherein the different switching patterns are associated with two or more of different frequencies, phases, duty cycles, and amplitudes with respect to each other to uniquely encode the x-ray radiation.

9. The apparatus of claim 1 wherein the decoupler determines an intensity contribution from each of the at least two x-ray sources to the aggregate signal.

10. The apparatus of claim 1 further including a common oscillator and/or pattern generator that generates the different switching patterns.

11. The apparatus of claim 1 wherein one or more of the at least two x-ray sources includes a control grid that facilitates generating its switching pattern.

12. The apparatus of claim 1 wherein the decoupler employs at least one of a subtraction technique, a Fourier transformation, a wavelet decomposition, and a lock-in amplifier to decouple the at least one signal from the aggregate signal.

13. The apparatus of claim 1 wherein at least one of the different switching patterns includes a sequence of one of substantially square, sinusoidal, triangular, and sine pulses.

14. The apparatus of claim 1 wherein the aggregate signal is sampled as a function of a maximum tube switch frequency and a minimum difference between switching frequencies.

15. The apparatus of claim 1 wherein the primary and cross scatter radiation are detected during a cardiac CT scan.

16. The apparatus of claim 1 wherein the apparatus is one of medical imaging, animal imaging, non-destructive imaging, and industrial imaging tomographic apparatus.

17. A computed tomography (CT) reconstruction method comprising:
    encoding, with different switching patterns, individual radiation outputs of at least two concurrently activated x-ray sources that emit radiation into an imaging region during a same time period, wherein the switching patterns partially overlap;
    concurrently detecting radiation emitted by the at least two x-ray sources with at least one detector that detects radiation including uniquely encoded primary radiation from a corresponding one of the at least two x-ray sources and uniquely encoded cross scatter radiation from another of the other at least two x-ray sources;
    generating a composite signal that includes components indicative of the detected primary and cross scatter radiation;
    locating a primary radiation signal within the composite signal and associating the primary radiation signal with a corresponding one of the at least two x-ray tubes based on the switching patterns; and
    reconstructing the primary radiation signal to generate an image of a subject within the imaging region.

18. The method of claim 17 further including: locating a cross scatter radiation signal within the composite signal; associating the cross scatter radiation signal with a corresponding one of the at least two x-ray tubes based on the switching patterns; and reconstructing the cross scatter radiation signal.

19. The method of claim 17 further including generating each of the different switching patterns with a different switching frequency to frequency encode the x-ray radiation.

20. The method of claim 17 further including generating each of the different switching patterns with a different phase to phase encode the x-ray radiation.

21. The method of claim 17 further including encoding the x-ray radiation with different code patterns.

22. The method of claim 17 further including generating at least one of the different switching patterns with a duty cycle of greater than 50%.

23. The method of claim 17 further including using at least one of a subtraction technique, a Fourier transform, a lock-in amplifier, and a wavelet transform to decouple the primary radiation signal from the aggregate signal.

24. An apparatus comprising:
means for concurrently generating multiple uniquely encoded x-ray beams that traverse a same examination region during a same time period, wherein encoding patterns of the uniquely encoded x-ray beams partially overlap;
means for combining signals indicative of the x-ray beams; and
means for identifying at least one of the individual signals in the combined signal and associating it with a corresponding one of the x-ray sources.

* * * * *